(12) United States Patent
Liu et al.

(10) Patent No.: US 8,007,740 B2
(45) Date of Patent: Aug. 30, 2011

(54) REACTION CUVETTE WASH UNIT

(75) Inventors: Qisong Liu, Shenzhen (CN); Guochao Luo, Shenzhen (CN)

(73) Assignee: Shenzhen Mindray Bio-Medical Electronics Co., Ltd. (CN)

( * ) Notice: Subject to any disclaimer, the term of this patent is extended or adjusted under 35 U.S.C. 154(b) by 690 days.

(21) Appl. No.: 11/615,590

(22) Filed: Dec. 22, 2006

(65) Prior Publication Data

US 2008/0101990 A1  May 1, 2008

(30) Foreign Application Priority Data

Oct. 26, 2006  (CN) .......................... 2006 1 0063323

(51) Int. Cl.
| | |
|---|---|
| G01N 21/00 | (2006.01) |
| G01N 31/00 | (2006.01) |
| G01N 33/00 | (2006.01) |
| G01N 35/00 | (2006.01) |
| G01N 35/08 | (2006.01) |
| B01L 3/00 | (2006.01) |
| B01L 3/02 | (2006.01) |

(52) U.S. Cl. .......... 422/510; 422/63; 422/501; 422/509; 422/519; 436/43; 436/54; 73/864.01

(58) Field of Classification Search .................. 422/510, 422/519; 436/54
See application file for complete search history.

(56) References Cited

U.S. PATENT DOCUMENTS

| | | | | |
|---|---|---|---|---|
| 4,199,013 | A | * | 4/1980 | Reich et al. .................. 141/130 |
| 5,895,630 | A | * | 4/1999 | Skaborn et al. ............... 422/100 |
| 5,957,167 | A |   | 9/1999 | Feygin |
| 6,171,280 | B1 | * | 1/2001 | Imazu et al. .................. 604/118 |
| 6,270,726 | B1 | * | 8/2001 | Tyberg et al. ................. 422/100 |
| 6,363,802 | B1 | * | 4/2002 | Grippo et al. ............... 73/864.24 |
| 2005/0013744 | A1 | * | 1/2005 | Nagai et al. .................. 422/100 |

FOREIGN PATENT DOCUMENTS

| | | |
|---|---|---|
| CN | 1493862 | 11/2002 |
| CN | 2579535 | 11/2002 |
| CN | 2579535 Y | 10/2003 |
| FR | 2836846 A1 | 9/2003 |
| JP | 10-216667 A | 11/2006 |

OTHER PUBLICATIONS

Office action for Chinese application 200610063323.0 dated Jul. 10, 2009.
English Translation of Abstract for Foreign Patent Document CN2579535Y.
English Translation of Abstract for Foreign Patent Document FR2836846A1.

* cited by examiner

Primary Examiner — Jill Warden
Assistant Examiner — Charles D Hammond
(74) Attorney, Agent, or Firm — Vista IP Law Group, LLP.

(57) ABSTRACT

The invention discloses a reaction cuvette wash unit comprising a cleaning needle assembly, a straight guide pair, a slide screw pair, a motor, a trigger component associated with a cleaning needle of the cleaning needle assembly in a manner to move with that cleaning needle, and a sensor used to sense the position of the trigger component. When the trigger component moves to a predetermined position, the sensor is triggered and sends a signal to a controller such that the controller controls in a manner to stop the motor. Each of cleaning needle components further comprises a sheath holder and an elastic member. The elastic member is designed to provide an elastic contact while the cleaning needles touch the bottom surface of the reaction cuvette, such that a relatively small force is exerted upon the bottom of the reaction cuvette, thereby effectively protecting the reaction cuvette from damage.

10 Claims, 3 Drawing Sheets

REACTION CUVETTE WASH UNIT

STATEMENT OF RELATED APPLICATION

This application claims the priority of the Chinese patent application No. 200610063323.0, filed on Oct. 26, 2006, entitled "REACTION CUVETTE WASH UNIT", the disclosure of which is incorporated herein by reference in entirety.

FIELD OF THE INVENTION

The present invention relates to a wash unit for use in automated chemistry analyzer, and more particularly to a wash unit which functions cooperatively with a reaction tray in a manner to implement automatic cleaning of the reaction cuvette by a set of gas-liquid path system.

BACKGROUND OF THE INVENTION

The existing automatic wash unit for a full-automatic biochemical analyzer comprises a motor and multiple sets of cleaning needle components, at least one of which has a wipe nozzle. Driven by the motor, the wipe nozzle of the cleaning needle component gets access into the reaction cuvette while the reaction tray pauses, touches the bottom of the cuvette, and rises without the reaction cuvette after a rather short period of time, thereby fulfilling the cleaning of the reaction cuvette. However, this wash unit suffers from the following shortcomings. As there is no anticollision mechanism, the wipe nozzle may easily collide with the wall of the cuvette when it gets access into the reaction cuvette, thereby making the wipe nozzle, cleaning needles and the reaction cuvette damaged. Moreover, the existing structures are rather complicated. They either move unevenly, or fail to perform the power-off self-locking in the vertical direction, or are compromised by a high cost.

SUMMARY OF THE INVENTION

The object of the present invention is to provide a driving device and an anticollision protective device for a reaction cuvette wash unit, and to provide a reaction cuvette wash unit comprising the driving device and the anticollision protective device, which equipment is capable of effectively protecting the reaction cuvette and cleaning needles.

According to a first aspect of the present invention, there is provided a driving device for use in a reaction cuvette wash unit comprising: a straight guide pair, a sliding block of which is connected to a cleaning needle assembly so as to drive the cleaning needle assembly to move; a slide screw pair, a nut of which is connected to the sliding block so as to drive it to move along the guide; and a motor, an output shaft of which is connected to a lead screw in the slide screw pair so as to drive the lead screw to rotate. Wherein the connection concerned preferably is a rigid connection.

In the driving device for use in the reaction cuvette wash unit according to the first aspect of the present invention, preferably, the sum of the motor's power-off holding torque and the sliding lead screw's friction moment is greater than the countermoment generated by the gravity of the cleaning needle assembly. Thereby, it is possible to realize the power-off self-locking in the vertical direction. The motor therein is a step motor, and the lead screw in the slide screw pair is a sliding lead screw with steep-lead.

According to a second aspect of the present invention, there is provided an anticollision protective device for use in a reaction cuvette wash unit comprising: a trigger component, which is associated with one of cleaning needles in a cleaning needle assembly of the reaction cuvette wash unit in a manner to move with that cleaning needle; and a sensor for sensing the position of the trigger component. When the trigger component moves to a predetermined position, the sensor is triggered and sends a trigger signal to a controller such that the controller controls in a manner to stop a driving device of the reaction cuvette wash unit.

In the anticollision protective device for the reaction cuvette wash unit according to the second aspect of the present invention, preferably, the trigger component is a baffle plate; and the sensor is a photoelectric sensor, on which is provided an induction slot accessible to an end of the baffle plate. The predetermined position is a proper position to which the trigger component moves with cleaning needles when collision occurs to the cleaning needles.

According to a third aspect of the present invention, there is provided a reaction cuvette wash unit comprising: a cleaning needle assembly; a straight guide pair, a sliding block of which is connected to the cleaning needle assembly so as to drive the cleaning needle assembly to move; a slide screw pair, a nut of which is connected to the sliding block so as to drive it to move along the guide; a motor, an output shaft of which is connected to a lead screw in the slide screw pair so as to drive the lead screw to rotate; a trigger component, which is associated with one of cleaning needles in the cleaning needle assembly of the reaction cuvette wash unit in a manner to move with that cleaning needle; and a sensor for sensing the position of the trigger component. When the trigger component moves to a predetermined position, the sensor is triggered and sends a trigger signal to a controller such that the controller controls in a manner to stop a driving device of the reaction cuvette wash unit. The connection concerned is a rigid connection.

According to the third aspect of the present invention, the cleaning needle assembly comprises: several cleaning needles and needle sheaths each of which fixedly nests one of the cleaning needles; a supporter including an upper supporting plate and a lower supporting plate, on both of which a plurality of mounting holes are correspondingly provided for movably mounting the cleaning needles nested by the needle sheaths; sheath holders, secured to each of the needle sheaths and located at one side of the lower supporting plate facing the upper supporting plate, the sheath holders being provided with pinholes and locating pins to prevent the cleaning needles from rotating; and elastic members, each nesting one of the needle sheaths and being located between each of the sheath holders and the upper supporting plate, respectively. Wherein the trigger component is a baffle plate mounted on one of the sheath holders; and the sensor is a photoelectric sensor provided on the lower supporting plate, on which is provided with an induction slot accessible to an end of the baffle plate.

In the reaction cuvette wash unit according to the third aspect of the present invention, preferably, the elastic members are springs. A wipe nozzle is mounted on at least one of the cleaning needles. The sum of the motor's power-off holding torque and the sliding lead screw's friction moment is greater than the countermoment generated by the cleaning needle assembly's gravity, thereby fulfilling a power-off self-locking in the vertical direction. The motor concerned is a step motor, and the lead screw in the slide screw pair is a sliding lead screw with steep-lead. The predetermined position is a proper position to which the trigger component moves with cleaning needles when collision occurs to the cleaning needle.

The beneficial effect of the present invention is as follows.

(1) The driving device has a simple structure, operates reliably and realizes a power-off self-locking.

(2) The adoption of the elastic members provides an elastic contact while the cleaning needles touch the bottom surface of the reaction cuvette, such that a relatively small force is exerted upon the bottom of the reaction cuvette, thereby effectively protecting the reaction cuvette from damage.

(3) The provision of the baffle plate and sensor makes it possible that when the wipe nozzle collides with the inwall of the reaction cuvette, the controller could stop the motor and in turn stop the cleaning needles from continuous access, such that the wipe nozzle, cleaning needles and the reaction cuvette are under effective protection.

DETAILED DESCRIPTION OF THE INVENTION

Figure 1:
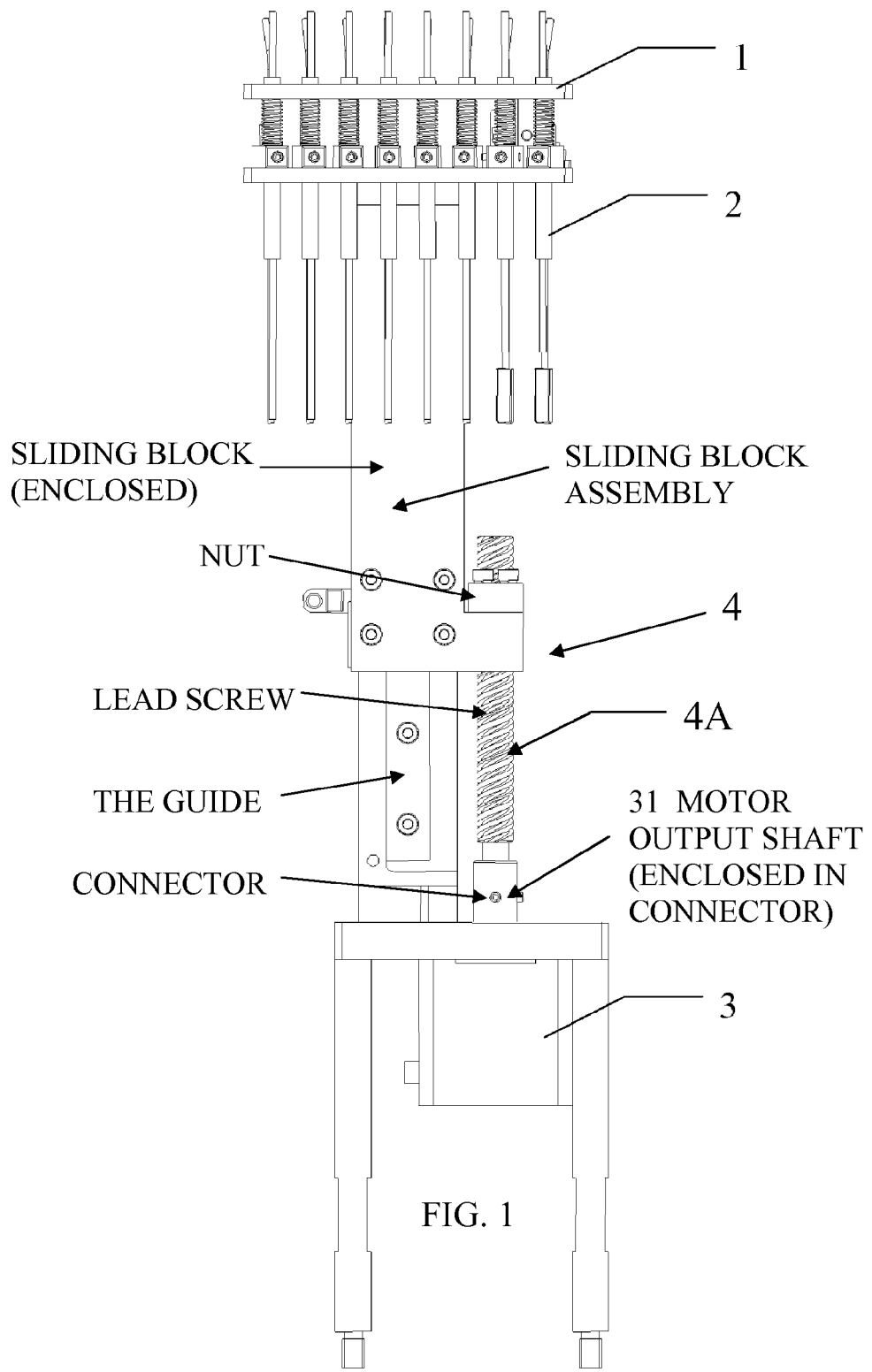
FIG. 1 is a front view of a reaction cuvette wash unit according to the present invention.
Figure 2:
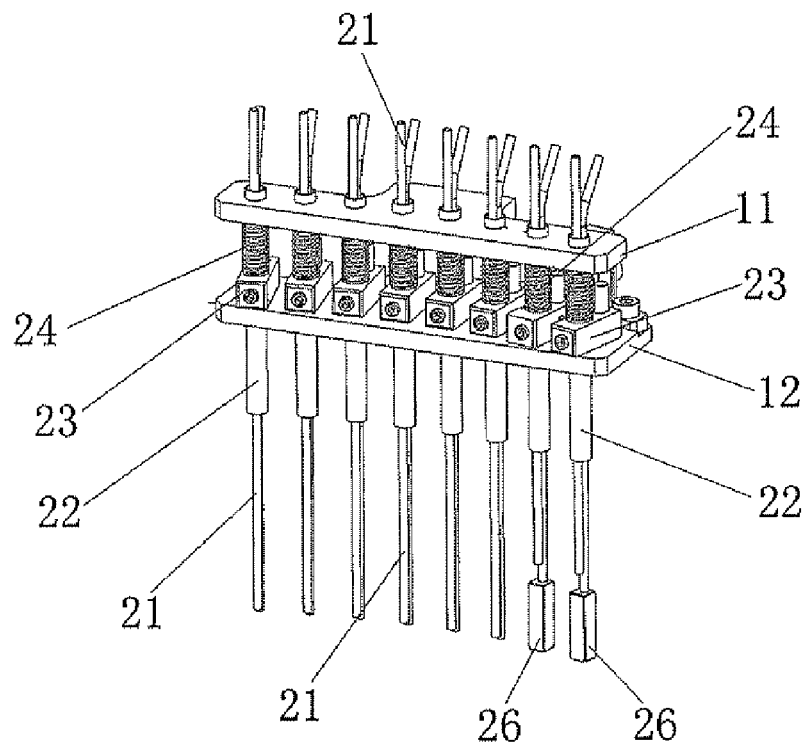
FIG. 2 is a stereogram of a cleaning needle assembly of the reaction cuvette wash unit according to the present invention, viewed from the front.
Figure 3:
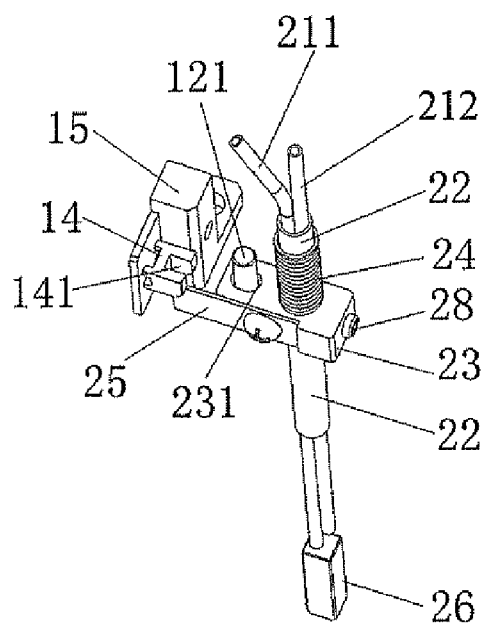
FIG. 3 is a schematic view of the partial structure of the cleaning needle assembly of the reaction cuvette wash unit according to the present invention.
Figure 4:
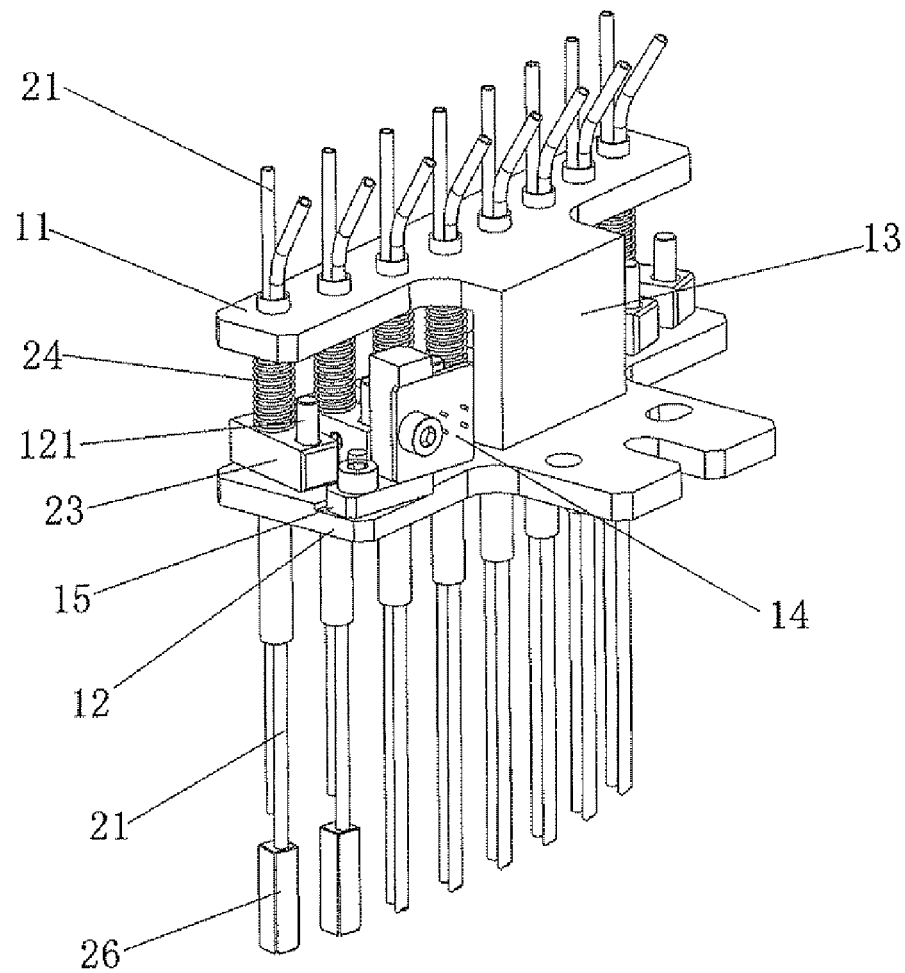
FIG. 4 is a stereogram of the cleaning needle assembly of the reaction cuvette wash unit according to the present invention, viewed from the back.

Referring to FIG. 1, in this embodiment, the reaction cuvette wash unit comprises a supporter 1 and eight sets of cleaning needle components 2 mounted on the support 1, a power unit 3 and a driving device 4. As shown in FIG. 2, the supporter 1 includes an upper supporting plate 11 and a lower supporting plate 12, which are both positioned horizontally and have a certain distance in height. The upper and lower plates 11 and 12 are fixedly joined as an integral part by a junction plate 13 positioned vertically, as shown in FIG. 4. The upper supporting plate 11 has eight upper mounting holes spaced thereon in a row, while the lower supporting plate 12 has eight lower mounting holes spaces thereon in a row. Eight upper mounting holes are aligned with those eight lower ones respectively, thus forming eight sets of mounting holes for mounting the cleaning needle components 2. The lower supporting plate 12 also provides eight locating pins 121 protruding upwardly, as shown in FIG. 3.

As shown in FIG. 2, eight sets of cleaning needle components 2 each comprise cleaning needles 21, a needle sheath 22 and a sheath holder 23. Each cleaning needle component 2 has two cleaning needles 21, which are an suction needle 211 and a drainage needle 212 respectively. The needle sheath 22 nests and adheres to the suction needle 211 and the drainage needle 212 by glue. The sheath holder 23 is fastened to the middle of the needle sheath 22 by a fastening screw 28, and has thereon a pinhole 231 at a position corresponding to the locating pin 121. These eight needle sheaths 22, which are fixedly joined with cleaning needles, fit with each of these eight sets of mounting holes in a manner like the fit of a shaft and a hole, and this fit pertains to a clearance fit, thereby enabling these eight needle sheaths to move up and down vertically with respect to the supporter (i.e. the direction of gravity). Eight locating pins 121 are inserted into eight sheath holders' pinholes 231 respectively, thus preventing cleaning needles from rotating. Each of the eight needle sheaths is nested by a spring 24, the upper end and the lower end of which sustain the upper supporting plate 11 and press against the corresponding sheath holder 23 respectively, while each of the sheath holders 23 in turn presses against the lower supporting plate 12. Because the dimension of each sheath holder 23 is greater than that of the corresponding lower mounting holes provided on the lower supporting plate 12, each of these cleaning needle components 2 would not disengage with the supporter 1 from the bottom under gravity.

The automatic cleaning process for the reaction cuvette requires that two cleaning needle component should have a wipe nozzle 26 mounted on each cleaning needle therein. Since the dimension of the wipe nozzle 26 approaches to that of the intracavity of the reaction cuvette, the gap between the wipe nozzle and the inwall of the reaction cuvette is rather small where the cleaning needles reach downward into the reaction cuvette. In order to protect the wipe nozzle, cleaning needles and the reaction cuvette, one of these two sets of cleaning needle components is provided with a baffle palte 25, which is fixedly mounted on one of the sheath holders 23. For this cleaning needle component, the baffle plate 25, the cleaning needles 21, the needle sheath 22 and the sheath holder 23 are fixedly joined as an integral part. The lower supporting plate 12 has thereon a photoelectric sensor 14 corresponding to the baffle plate 25. The photoelectric sensor 14 including an induction slot 141 is fixed on a sensor mounting holder 15 which is further secured to the lower supporting plate 12, as shown in FIG. 3 and FIG. 4. The induction slot 141 of the photoelectric sensor is located in the pathway of the vertical up-and-down movement of the baffle plate 25. That is, the projection of the baffle plate 25 on the horizontal plane is at least partially within the projection of the induction slot 141 on that plane. At the initial position, the induction slot 141 is located above the baffle plate 25.

The reaction cuvette wash unit further comprises a power unit 3 and a driving device 4, in which the power unit 3 is a step motor and the driving device 4 is a slide screw pair. The output shaft 31 of the step motor 3 is rigidly connected to the input end of the driving device 4 (i.e., one end of the lead screw in the slide screw pair), and the output end of the driving device 4 (i.e., the other end of the lead screw in the slide screw pair) is rigidly connected to the sliding block in the straight guide pair. The cleaning needle assemblies are also rigidly connected to the sliding block. Thus, the step motor can drive the cleaning needle assembly to move up and down via the driving device, such that the cleaning needles get access into the reaction cuvette while the reaction tray pauses and touch the bottom of the reaction cuvette, and rise from the bottom without the reaction cuvette after a short period of time (i.e., cleaning the reaction cuvette).

Figure 5:
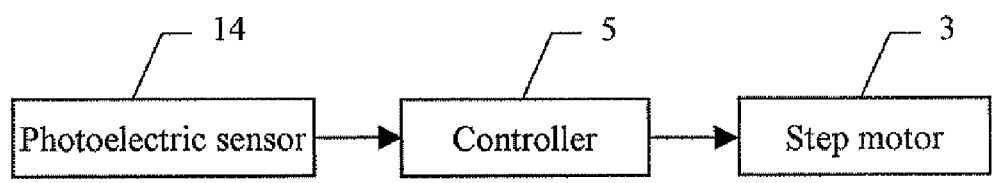
FIG. 5 is a block diagram of the control principle of the reaction cuvette wash unit according to the present invention.

While the cleaning needles are being inserted into the reaction cuvette, if an accident happens to the cleaning needles, resulting in collision between the wipe nozzle and the reaction cuvette, the wipe nozzle is given an upward force, which would push the baffle plate 25 along with the entire cleaning needle component up for a long distance. This enables the baffle plate 25 to go into the induction slot 141 of the photoelectric sensor and trigger the photoelectric sensor 14. The photoelectric sensor then sends a signal to a controller 5, as shown in FIG. 5. The controller 5 outputs a control signal to stop the step motor 3, and in turn stop the cleaning needles 21 from continuous access, thereby protecting the wipe nozzle, cleaning needles and the reaction cuvette. Because the relative position between each set of cleaning needles is fixed, as long as one of them encounters collision, the other cleaning needles inevitably collide. Hence, it suffices to establish a baffle plate on only one cleaning needle component, in order for all eight cleaning needle components to fulfill the anticollision function.

The present invention has been described hereinabove in greater details with reference to the preferred embodiments. However, the invention shall not be interpreted to be limited to these specific embodiments. Those of ordinary skill in the art will appreciate that some simple derivations or substitutions could be made without departing from the scope and spirit of the present invention, which shall be considered as falling into the protection scope defined by the appended claims.

What is claimed is:

1. A reaction cuvette wash unit, comprising:
   a cleaning needle assembly which comprises at least one cleaning needle for cleaning its respective reaction cuvette, wherein the cleaning needle assembly comprises:
      a plurality of cleaning needles and one or more needle sheaths, each of which encloses at least a part of one of one of the plurality of cleaning needles;
      a supporter including an upper supporting plate and a lower supporting plate, each of which defines a plurality of respective mounting holes that are correspondingly provided for movably mounting the plurality of cleaning needles;
      one or more sheath holders, each of which is secured to one of the one or more needle sheaths defines at least one pinhole and at least one locating pin to prevent the plurality of cleaning needles from rotating; and
      one or more elastic members which enclose at least part of each of the one or more needle sheaths and is located between each of the one or more sheath holders and the upper supporting plate;
   a straight guide pair which comprises a sliding block and a guide, wherein the sliding block is connected to the cleaning needle assembly to cause the cleaning needle assembly to move;
   a driving device which is connected to the sliding block so as to cause the sliding block to move along an axis of the guide;
   a motor, an output shaft of which is connected to a lead screw in the driving device so as to drive the lead screw to move at least one of a plurality of cleaning needles in the cleaning needle assembly to or from a cleaning position to clean a respective cuvette;
   a trigger component, which is associated with the at least one cleaning needle in a manner to move with the at least one cleaning needle;
   a sensor for sensing the position of the trigger component, wherein the motor is operatively coupled to the sensor, and when the trigger component moves or is caused to move to a position, the sensor is triggered and sends a trigger signal to stop the motor from driving the driving device of the reaction cuvette wash unit to prevent the at least one cleaning needle from being further driven into the respective cuvette in the reaction cuvette wash unit.

2. The reaction cuvette wash unit according to claim 1, wherein
   the trigger component comprises a baffle plate mounted on one of the one or more sheath holders; and
   the sensor comprises a photoelectric sensor operatively attached to the lower supporting plate which defines an induction slot that is used to accommodate an end of the baffle plate.

3. The reaction cuvette wash unit according to claim 1, wherein the one or more elastic members comprises one or more springs.

4. The reaction cuvette wash unit according to claim 1, wherein a wipe nozzle is mounted on at least one of the plurality of cleaning needles.

5. The reaction cuvette wash unit according to claim 1, wherein a sum of a power-off holding torque of the motor and friction between the lead screw and one or more of its mating parts overcomes a force generated by a weight of the cleaning needle assembly so as to fulfill a power-off self-locking in the vertical direction.

6. The reaction cuvette wash unit according to claim 1, wherein the motor comprises a step motor.

7. The reaction cuvette wash unit according to claim 1, wherein the lead screw in the driving device comprises a sliding lead screw with a long lead.

8. The reaction cuvette wash unit according to claim 1, wherein the driving device is rigidly connected to the straight guide pair.

9. The reaction cuvette wash unit according to claim 1, wherein the position comprises a position to which the trigger component moves relatively to the one or more cleaning needles when collision occurs between at least one of the one or more cleaning needles and at least one respective cuvette.

10. The reaction cuvette wash unit of claim 1, wherein the position corresponds to a location to which the trigger component moves or is caused to move on a sidewall of the respective cuvette.

\* \* \* \* \*